United States Patent [19]

Berthold

[11] 4,361,562
[45] Nov. 30, 1982

[54] 3-AMINOPROPOXYARYL DERIVATIVES, THEIR PREPARATION AND PHARMACEUTICAL COMPOSITIONS CONTAINING THEM

[75] Inventor: Richard Berthold, Bottmingen, Switzerland

[73] Assignee: Sandoz Ltd., Basel, Switzerland

[21] Appl. No.: 175,260

[22] Filed: Aug. 4, 1980

[30] Foreign Application Priority Data

Aug. 10, 1979 [CH] Switzerland .................. 7366/79
Aug. 10, 1979 [CH] Switzerland .................. 7368/79
Feb. 7, 1980 [CH] Switzerland .................. 987/80

[51] Int. Cl.³ .............. C07D 31/405; C07D 31/445; C07D 31/495; A61K 403/12; A61K 401/12
[52] U.S. Cl. .................................... 424/250; 544/373; 546/201; 424/256; 424/274; 548/505
[58] Field of Search ............... 544/373, 363; 424/250, 424/274, 256; 546/201; 260/326.15, 326.14 R, 326.14 D

[56] References Cited

U.S. PATENT DOCUMENTS

| 3,051,709 | 8/1962 | Shapiro et al. ............ 564/349 |
| 3,253,034 | 5/1966 | McLoughlin ............ 260/570.6 |
| 3,337,628 | 8/1967 | Crowther et al. ............ 564/349 |
| 3,696,120 | 10/1972 | Troxler et al. ............ 260/326.14 R |
| 3,888,898 | 6/1975 | Koppe et al. ............ 564/349 |
| 4,038,279 | 7/1977 | Renth et al. ............ 544/363 |
| 4,080,463 | 3/1978 | Troxler et al. ............ 260/326.14 R |
| 4,080,463 | 3/1978 | Troxler ............ 260/326.14 R |
| 4,229,464 | 10/1980 | Kampe et al. ............ 260/326.14 R |

FOREIGN PATENT DOCUMENTS 2302717 1/1973 Fed. Rep. of Germany ...... 546/201
2337461 2/1975 Fed. Rep. of Germany .
1410783 1/1972 United Kingdom ............... 546/201

OTHER PUBLICATIONS

Brit. J. Pharmac., (1974), 51, 441–446, E. Müller—Schweinitzer & E. Stürmer.

Primary Examiner—Donald G. Daus
Assistant Examiner—Sharon A. Gibson
Attorney, Agent, or Firm—Gerald D. Sharkin; Robert S. Honor

[57] ABSTRACT

The compounds of formula I

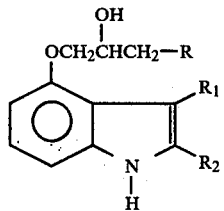

where $R_1$, $R_2$ and R have various significances, and physiologically acceptable hydrolyzable derivatives thereof having the hydroxy group in the 2 position of the 3-aminopropoxy side chain in esterified form, are useful as cardiotonic, anti-arrhythmic, α- and β-adrenoceptor blocking agents.

29 Claims, No Drawings

3-AMINOPROPOXYARYL DERIVATIVES, THEIR PREPARATION AND PHARMACEUTICAL COMPOSITIONS CONTAINING THEM

The present invention relates to 3-aminopropoxyaryl derivatives, their preparation and pharmaceutical compositions containing them.

In accordance with the invention there are provided compounds of formula I,

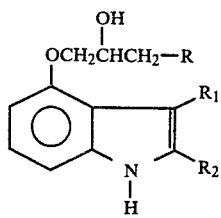

wherein
$R_1$ is hydrogen or methyl,
$R_2$ is hydrogen, methyl, hydroxymethyl, carboxyl, alkoxycarbonyl of 2 to 5 carbon atoms, carbamoyl or cyano and
R is:
(a) a group $-B-CO-R_h$, wherein B is a group (i), (ii) or (iii), groups (i), (ii) and (iii) having the following significances:

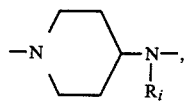

wherein
$R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;

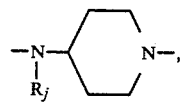

wherein $R_j$ is hydrogen or alkyl of 1 to 4 carbon atoms;

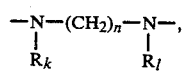

wherein
n is 2, 3 or 4,
$R_k$ is hydrogen or alkyl of 1 to 4 carbon atoms and
$R_l$ has the significance indicated above for $R_j$, and
$R_h$ is phenylalkyl of 7 to 11 carbon atoms or diphenylalkyl of 13 to 17 carbon atoms, any of the phenyl rings of these two radicals optionally being mono- or independently disubstituted by alkyl of 1 to 4 carbon atoms, alkoxy of 1 to 4 carbon atoms or halogen of atomic number of from 9 to 35;
(b) a group

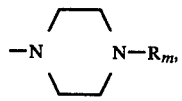

wherein
$R_m$ is $-COR_n$ or $-R_p$, wherein
$R_n$ has the significance indicated above for $R_h$ and
$R_p$ is phenyl monosubstituted by alkoxy of 1 to 4 carbon atoms or halogen of atomic number of from 9 to 35, phenyl independently disubstituted by alkyl of 1 to 4 carbon atoms, alkoxy of 1 to 4 carbon atoms or halogen of atomic number of from 9 to 35, phenylalkyl of 7 to 11 carbon atoms or diphenylalkyl of 13 to 17 carbon atoms, any of the phenyl rings of these last two radicals optionally being mono- or independently disubstituted by alkyl of 1 to 4 carbon atoms, alkoxy of 1 to 4 carbon atoms or halogen of atomic number of from 9 to 35, with the provisos that,
(a) when $R_1$ and $R_2$ are hydrogen
then $R_p$ is other than ring substituted or unsubstituted phenethyl and
(b) when $R_1$ is hydrogen and $R_2$ is hydrogen, carboxyl or alkoxycarbonyl of 2 to 5 carbon atoms,
then $R_p$ is other than monosubstituted phenyl,
and physiologically acceptable hydrolyzable derivatives thereof having the hydroxy group in the 2 position of the 3-aminopropoxy side chain in esterified form.

A group of compounds of the invention is the compounds of formula Ip,

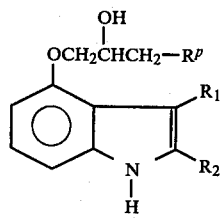

wherein
$R_1$ and $R_2$ are as defined above and
$R^p$ is:
(a) a group $-B-CO-R_h$, as defined above;
(b) a group

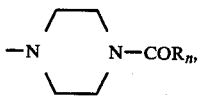

wherein $R_n$ is as defined above,
and physiologically acceptable hydrolyzable derivatives thereof having the hydroxy group in the 2 position of the 3-aminopropoxy side chain in esterified form.

Another group of compounds of the invention is the compounds of formula Ip',

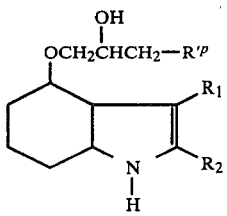

wherein
R₁ and R₂ are as defined above and
$R_p'$ is a group

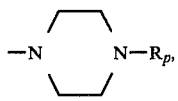

wherein $R_p$ is as defined above, including the provisos thereto,
and physiologically acceptable hydrolyzable derivatives thereof having the hydroxy group in the 2 position of the 3-aminopropoxy side chain in esterified form.

Conveniently $R_p$ in formula Ip' is substituted phenyl, or is unsubstituted or substituted benzyl or diphenylmethyl.

Another group of compounds of the invention is the compounds of formula Ia,

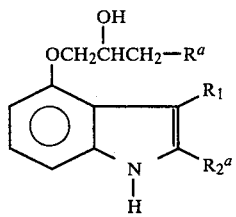

wherein
R₁ is as defined above,
$R_2^a$ is methyl, alkoxycarbonyl of 2 to 5 carbon atoms, carbamoyl or cyano and
$R^a$ is:
(a) a group $-B^a-CO-R_h^a$,
wherein
$R^a$ is a group

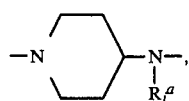

wherein $R_i^a$ is hydrogen, methyl, phenyl or halophenyl and
$R_h^a$ is benzyl or diphenylmethyl;
(b) a group

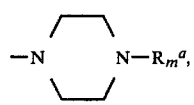

wherein $R_m^a$ is $-COR_n^a$ or $-R_p^a$, wherein $R_n^a$ is diphenylmethyl and $R_p^a$ is diphenylmethyl or 2,2-diphenylethyl.

Another group of compounds of the invention is the compounds of formula Ib,

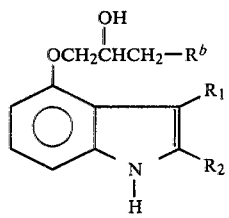

wherein
R₁ and R₂ are as defined above and
$R^b$ is:
(a) a group $B^b-CO-R_h$, wherein $B^b$ is a group (i'), (ii) or (iii), wherein groups (ii) and (iii) are as defined above and group (i') has the following significance:

(i')

wherein $R_i^b$ is hydrogen or alkyl of 1 to 4 carbon atoms, and
$R_h$ is as defined above, or
(b) a group

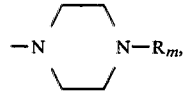

wherein $R_m$ is $-COR_n$ or $-R_p$,
wherein $R_n$ and $R_p$ are as defined above, with the provisos that,
(a) when R₁ and R₂ are hydrogen,
then $R_p$ is other than ring substituted or unsubstituted phenethyl and
(b) when R₁ is hydrogen and R₂ is hydrogen, carboxyl or alkoxycarbonyl of 2 to 5 carbon atoms,
then $R_p$ is other than monosubstituted phenyl, and physiologically acceptable hydrolyzable derivatives thereof having the hydroxy group in the 2 position of the 3-aminopropoxy side chain in esterified form.

In a subgroup $R_h$ in formula Ib is unsubstituted or substituted diphenylalkyl. In another subgroup R₂ is other than hydrogen. In another subgroup R₂ is cyano. In another subgroup R₁ is hydrogen. In another subgroup $R^b$ is a group

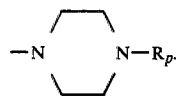

Another group of compounds of the invention is the compounds of formula Ic,

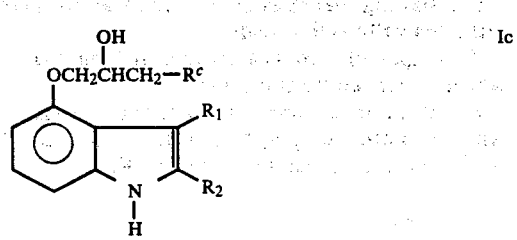

wherein
R$_1$ and R$_2$ are as defined above and
R$^c$ is:
(a) a group B$^b$—CO—R$_h^b$, wherein
B$^b$ is as defined above and
R$_h^b$ is diphenylalkyl of 13 to 17 carbon atoms, any of the phenyl rings of this radical optionally being mono- or independently disubstituted by alkyl of 1 to 4 carbon atoms, alkoxy of 1 to 4 carbon atoms or halogen of atomic number of from 9 to 35;
(b) a group

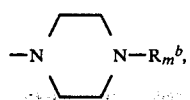

wherein
R$_m^b$ is —COR$_n^b$ or —R$_p^b$, wherein
R$_n^b$ and R$_p^b$ have the significance indicated above for R$_h^b$, and physiologically acceptable hydrolyzable derivatives thereof having the hydroxy group in the 2 position of the 3-aminopropoxy side chain in esterified form.

In a subgroup R$_2$ in formula Ic is other than hydrogen. In another subgroup R$_2$ is cyano. In another subgroup R$^c$ is a group

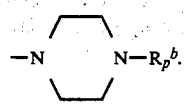

In another subgroup R$_1$ is hydrogen.

Physiologically hydrolyzable derivatives are those derivatives which under physiological conditions are split to the corresponding compounds having a hydroxy group in the 2 position of the 3-aminopropoxy side chain.

A group of derivatives in esterified form of the compounds of formula I is e.g. the compounds of formula E,

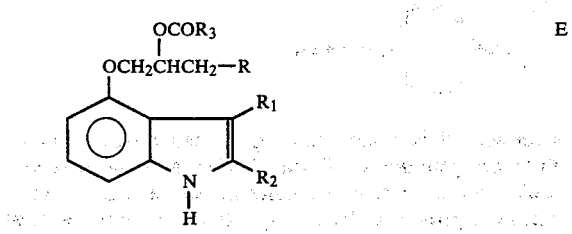

wherein
R$_1$, R$_2$ and R are as defined above, and
R$_3$ is alkyl of 1 to 12 carbon atoms, cycloalkyl of 3 to 7 carbon atoms, phenyl, phenylalkyl of 7 to 12 carbon atoms, phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

Preferred are the compounds wherein the hydroxy group in the 2 position of the 3-aminopropoxy side chain is in free form.

R$_1$ preferably is hydrogen, R$_2$ preferably is alkoxycarbonyl, carbamoyl or cyano, especially cyano. R preferably is a group

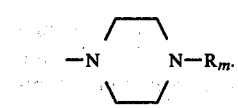

B preferably is a group (i)—R$_i$ and/or R$_l$ preferably are hydrogen or alkyl, especially hydrogen. R$_j$ and/or R$_k$ preferably are hydrogen. R$_h$, R$_n$ and/or R$_p$ preferably are substituted or unsubstituted diphenylalkyl. R$_m$ preferably is —R$_p$. n preferably is 2.

Phenylalkyl preferably is of 7 to 9 carbon atoms, especially 7 or 8 carbon atoms. When it is of more than 8 carbon atoms, the alkylene moiety thereof preferably is branched, especially in the α-position, was e.g. in the moieties

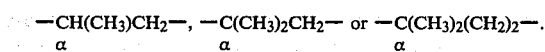

Diphenylalkyl preferably is of 13 to 15 carbon atoms, especially of 13 carbon atoms. The phenyl rings preferably are attached to the same carbon atom. They preferably are attached to the carbon atom in the ω-position, as e.g. in the 3-diphenylpropyl. Diphenylalkyl preferably is diphenylmethyl.

Alkyl (except as indicated herein under for R$_3$) and/or alkoxy preferably are of 1 or 2, especially 1 carbon atom. Alkoxycarbonyl preferably is of 2 or 3, especially 2 carbon atoms. When it is of more than 2 carbon atoms, it is preferably branched in the position α to the carbonyl moiety, as in isopropoxycarbonyl. Halogen preferably is chlorine or bromine, especially chlorine.

When R$_3$ is alkyl, it preferably is of 3 to 5 carbon atoms and preferably is branched, especially in the position α to the carbonyl group to which it is bound, as e.g. in isopropyl, tert-butyl and 3-pentyl, and especially tert-butyl. Cycloalkyl preferably is of 5 or 6 carbon atoms.

When it can be either substituted or unsubstituted, a phenyl ring preferably is unsubstituted. When a phenyl ring is substituted, it preferably is monosubstituted. When it is monosubstituted, the substituent preferably is in the para position. When it is disubstituted, the substituents preferably are in the meta and para positions. When it is polysubstituted, the substituents preferably are identical.

In accordance with the invention, a compound of the invention may be obtained by a process comprising reacting a corresponding compound of formula II,

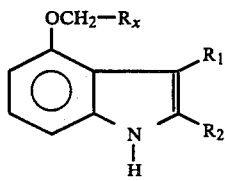

wherein $R_1$ and $R_2$ are as defined above, and $R_x$ is a group capable of reacting with a primary or secondary amine to give a 2-amino-1-hydroxyethyl group, with an appropriate compound of formula III,

R—H   III wherein R is as defined above, and, where required, appropriately esterifying the 2 position of the 3-aminopropoxy side chain in the resulting compound of formula I.

The amination process may be effected in conventional manner for the production of analogous 3-amino-2-hydroxypropoxyaryl compounds. For example, $R_x$ may be a group of formula

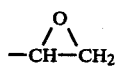

or a derivative of this group, e.g. a group of formula —CH(OH)—CH$_2$Y, wherein Y is chlorine, bromine or a group $R_y$—SO$_2$—O—, wherein $R_y$ is phenyl, tolyl or lower alkyl. Y is especially chlorine. The reaction is preferably effected in isopropanol or in an appropriate ether such as dioxane. Optionally an excess of the amine may be used as solvent. Alternatively, the reaction may be effected in a fusion melt. Suitable reaction temperatures may be from about 20° to about 200° C., conveniently the reflux temperature of the reaction mixture when a solvent is present.

The optional substitution of the 2-hydroxy group in the side chain may be effected in conventional manner. For example, it may be esterified in manner known for the production of analogous esters of 3-amino-2-hydroxypropoxyaryl compounds, if necessary using selective reactions when other reactive groups are present. When $R_2$ is hydroxymethyl or carbamoyl, such esterification step is effected selectively in the 2 position of the 3-amino-propoxy side chain, conveniently under temporary protection of the other reactive group or groups that may be present, e.g. for hydroxy in the form of e.g. a benzyloxy group, and subsequent selective splitting of the protecting group, e.g. by hydrogenation.

Free forms of the compounds of the invention may be converted into salt forms in conventional manner and vice versa. Suitable acids for acid addition salt formation include maleic, malonic and fumaric acid. When $R_2$ is carboxyl, salts may also be formed with strong bases, e.g. sodium hydroxide.

In the compounds of the invention, the carbon atom in e.g. the 2 position of the 3-aminopropoxy side chain is asymmetrically substituted. The compounds may thus exist in the racemic form or in individual optical isomer form. The preferred optical isomer has the S configuration at this asymmetrically substituted carbon atom of the 3-aminopropoxy side chain.

Individual optical isomer forms may be obtained in conventional manner, for example by using optically active starting materials or by fractional crystallisation using optically active acids.

A compound used as a starting material may be obtained in conventional manner.

In particular, a compound of formula II may be obtained by introducing by O-alkylation a group —OCH$_2$—$R_x$ into a compound of formula IV,

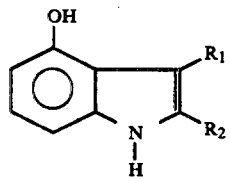

wherein $R_1$ and $R_2$ are as defined above. A compound of formula IV preferably is reacted in anionic form.

A compound of formula IIIa,

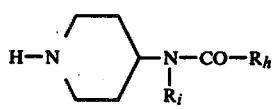

wherein $R_i$ and $R_h$ are as defined above, may be obtained by reacting a compound of formula,

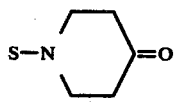

wherein S is a protecting group, e.g. a benzyl group, with hydroxylamine, reducing the resultant oxime, —appropriately monoacylating the resultant amine and, if desired, subsequently introducing a group $R_i$ by N-alkylation into the resultant monoacylated derivative, and finally splitting off the protecting group S from the resultant derivative.

A compound of formula IIIb

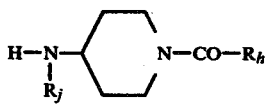

wherein $R_h$ and $R_j$ are as defined above, may be obtained by introducing one or, if desired, two protecting group(s), e.g. benzyl, into a compound of formula V,

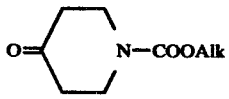

wherein Alk is lower alkyl, e.g. by reductive amination with benzylamine or dibenzylamine and, when a secondary amine has been produced, subsequently introducing a group $R_i$ by N-alkylation into the resultant amine, splitting off the group —COOAlk from the resultant tertiary amine, e.g. by decarboxylating hydrolysis, appropriately acylating the resultant cyclic amine and deprotecting the resultant acylated compound, e.g. by debenzylation.

A compound of formula IIIc,

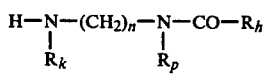

wherein $R_k$, $R_l$ and $R_h$ are as defined above, may be obtained by appropriately monoacylating a corresponding diamine.

A compound of formula IIId,

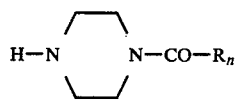

wherein $R_n$ is as defined above, may be obtained by appropriately acylating a compound of formula VI,

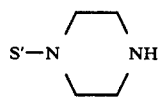

wherein S' is a protecting group, e.g. benzyl, and deprotecting the resultant acyl derivative, e.g. by debenzylation.

Insofar as the preparation of any particular starting material is not particularly described, this may be effected in conventional manner.

In the following Examples all temperatures are in degrees Centigrade and are uncorrected.

EXAMPLE 1

4-[3-(4-diphenylmethylpiperazin-1-yl)-2-hydroxypropoxy]-1H-indol-2-carbonitrile 4 g of 4-(2,3-epoxypropoxy)-1H-indol-2-carbonitrile and 3.7 g of 1-diphenylmethylpiperazine are dissolved in methanol and the solvent is evaporated to dryness. The residue is heated to 70° for 10 minutes. After cooling to room temperature the resultant yellow oil is dissolved in ethanol and an equivalent of malonic acid is added. After addition of ether to the ethanolic solution crystallization begins. The hydrogen malonate form of the title compound is obtained in crystals containing ethanol (M.P. 124° [dec.]; M.P. after removal of the ethanol: 140°; M.P. of the methane sulfonate form: 188°; M.P. of the free base form: 163°–164°).

From the appropriate compound of formula II, wherein $R_x$ is

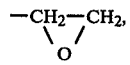

the following compounds of formula I may be obtained by reaction with the appropriate compound of formula III in analogous manner to Example 1:

| Example No. | R | $R_1$ | $R_2$ | | M.P. |
|---|---|---|---|---|---|
| 2 | 4-diphenylmethylpiperazin-1-yl | H | $CH_3$ | b | 172–174° |
| 3 | 4-diphenylacetylaminopiperidin-1-yl | H | CN | b | 153–154° |
| 4 | d-(N—diphenylacetyl-N—methylamino)-piperidin-1-yl | H | CN | ch | 180–181° |
| 5 | 4-diphenylacetylpiperazin-1-yl | H | CN | b | 119° (dec.) |
| 6 | 4-[N—(4-chlorophenyl)-N—phenylacetylamino]piperidin-1-yl | H | CN | b | 171–173° |
| 7 | 4-(diphenylmethyl)piperazin-1-yl | $CH_3$ | CN | b | 186–188° |
| 8 | 4-(diphenylmethyl)piperazin-1-yl | H | $CONH_2$ | b | 115° |
| 9 | 4-(diphenylmethyl)piperazin-1-yl | H | $COOCH_2CH_3$ | b | 130–132° |
| 10 | 4-(2,2-diphenylethyl)piperazin-1-yl | H | CN | zml | 195–197° | b = in free form
cn = in hydrochloride form
zml = in bis[base]hydrogen maleate form
dec. = decomposition The following compounds of formula I may also be obtained in a manner analogous to Example 1:

| Ex. | R | | $R_1$ | $R_2$ |
|---|---|---|---|---|
| R = group (a) | | | | |
| B = group (i) | | | | |
| A | 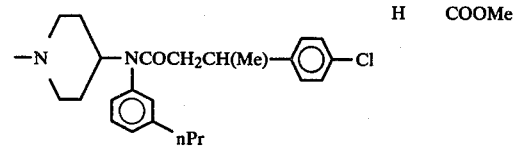 | | H | COOMe |

-continued
| Ex. | R | $R_1$ | $R_2$ |
|---|---|---|---|
| B | 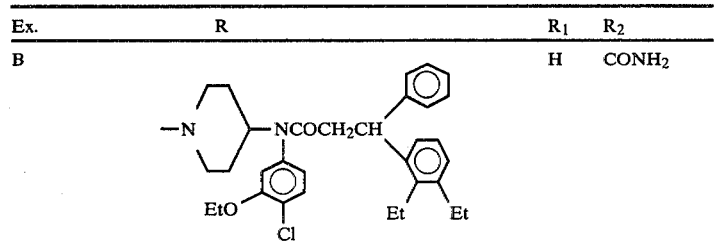 | H | $CONH_2$ |
| C | 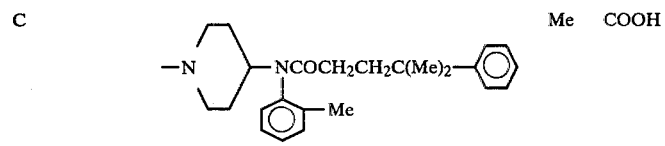 | Me | COOH |
| D | 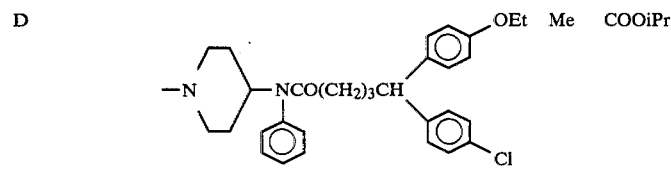 | Me | COOiPr |
B = group (ii)
| Ex. | R | $R_1$ | $R_2$ |
|---|---|---|---|
| E | 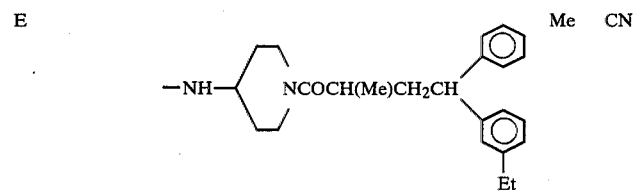 | Me | CN |
| F | 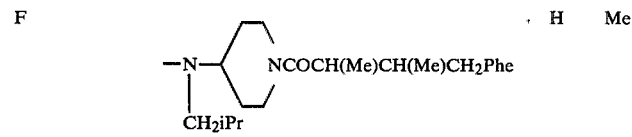 | H | Me |
B = group (iii)
| Ex. | R | $R_1$ | $R_2$ |
|---|---|---|---|
| G |  —N(iPr)(CH$_2$)$_2$NHCOCHPhe$_2$ | H | $CH_2OH$ |
| H | 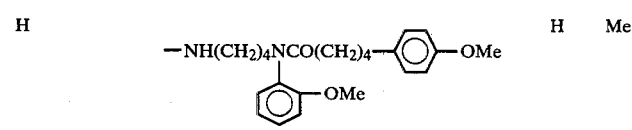 | H | Me |
R = group (b)
$R_m = COR_n$
| Ex. | R | $R_1$ | $R_2$ |
|---|---|---|---|
| I | 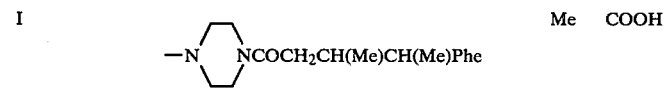 | Me | COOH |
| J | 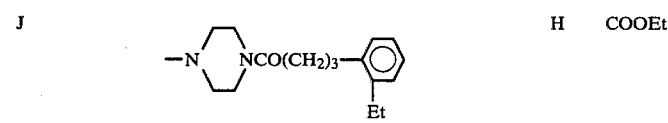 | H | COOEt |
| K | 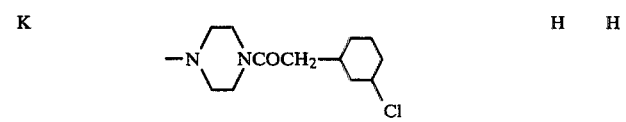 | H | H |

-continued

| Ex. | R | $R_1$ | $R_2$ |
|---|---|---|---|
| L | −N(piperazine)CO(CH₂)₄CH(cyclohexyl)(cyclohexyl-OMe) | Me | COOnBu |

$R_m = -R_p$

| Ex. | R | $R_1$ | $R_2$ |
|---|---|---|---|
| M | −N(piperazine)N−(cyclohexyl-OsBu) | H | $CONH_2$ |
| N | −N(piperazine)N−(cyclohexyl-Br) | Me | $CH_2OH$ |
| O | −N(piperazine)N−(cyclohexyl-OMe, Et) | Me | CN |
| P | −N(piperazine)N−(cyclohexyl-Me, Cl) | H | Me |
| Q | −N(piperazine)NCH₂CH(Me)CH₂Phe | Me | $CH_2OH$ |
| R | −N(piperazine)NCH₂CH₂CHPhe₂ | Me | Me |
| S | −N(piperazine)NCH₂C(Me)₂CH₂−Ph | H | COOMe |
| T | −N(piperazine)NCH₂CH₂CH(Me)CH(Ph)(Ph) | H | CN |
| U | −N(piperazine)NCH₂−(Ph-Br) | H | COOnPr |

-continued

| Ex. | R | $R_1$ | $R_2$ |
|-----|---|-------|-------|
| V | —N(piperazinyl)NCH₂CH(Phe)(Phe-F) | Me | CONH₂ | tBu = —C(CH₃)₃
nBu = —(CH₂)₃CH₃
sBu = —CH₂CH(CH₃)₂
Et = —CH₂CH₃
Me = —CH₃

Phe = —(phenyl ring)

iPr = —CH(CH₃)₂
nPr = —CH₂CH₂CH₃

The following derivatives, esters of the compounds of formula I (which are compounds of formula E) may be obtained by appropriately esterifying the 2 position of the 3-aminopropoxy side chain in the corresponding compounds of formula I ($R_1$, $R_2$ and R are as for the corresponding compound of formula I):

| Ex. No. | Corresp. compound of formula I (Example No.) | $R_3$ (Formula E) |
|---------|----------------------------------------------|-------------------|
| R = group (a) | | |
| 3-E1 | 3 | n-nonyl |
| 3-E2 | 3 | ethyl |
| 3-E3 | 3 | 3-ethylbenzyl |
| 4-E1 | 4 | 3-methyl-4-(3,4,5-tri-ethoxyphenyl)butyl |
| 4-E2 | 4 | cyclobutyl |
| 4-E3 | 4 | cycloheptyl |
| 6-E1 | 6 | 2-fluoro-3-chlorophenyl |
| 6-E2 | 6 | 5-phenylpentyl |
| R = group (b) | | |
| 1-E1 | 1 | n-nonyl |
| 1-E2 | 1 | ethyl |
| 1-E3 | 1 | 3-ethylbenzyl |
| 2-E1 | 2 | 3-methyl-4-(3,4,5-tri-ethoxyphenyl)butyl |
| 2-E2 | 2 | cyclobutyl |
| 2-E3 | 2 | cycloheptyl |
| 5-E1 | 5 | 2-fluoro-3-chlorophenyl |
| 5-E2 | 5 | 5-phenylpentyl |

The compounds of the invention are useful because they exhibit pharmacological activity in animals.

The compounds possess cardiotonic activity, as indicated by standard tests. For example, in the normotonic Numal anaesthetized dog, an increase in the contractile force of the left ventricle is observed upon intravenous administration of from about 0.2 to about 2 mg/kg and upon intraduodenal administration of from about 0.02 to about 2 mg/kg.

Dogs of either sex weighing from 10 to 15 kg are used. Numal in a dosis of 65 mg/kg i.v. is used as an anaesthetic. The animal is attached in supine position on the operation table. After the usual preparations have been effected, a heparinized catheter is introduced along the Arteria carotis dextra into the left ventricle under radiologic control and the transmission of the pressure is registered with a donor membrane (Gould Statham P 23 Gb). The increase in pressure as a function of time is computed and registered with an HSE-physiodifferentiator. The pressure increase in the left ventricle is a measure of the contractile force of the heart. The magnitude of the pressure differential is indicated in mm $Hg/_{sec}$. A suitable body temperature (about 36° to 37° C.) is maintained constant. After a control period of about 40 minutes the test substance is injected into the Vena fermoralis and its effect on the registered or computed parameters observed.

The compounds are therefore useful as cardiotonic agents, e.g. for the treatment of heart insufficiency.

Preferred in this indication is the compound of Example 1.

For the above-mentioned cardiotonic use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained relase form. For the larger mammals, the total daily dosage is in the range of from about 1 mg to about 500 mg, and dosage forms suitable for oral administration comprise from about 0.25 mg to about 250 mg of the compounds admixed with a solid or liquid pharmaceutical carrier or diluent. An example of a daily dosage is from 10 to 500 mg.

The compounds also exhibit antiarrhythmic activity, as indicated in standard tests. For example, they prolong the functional refractory period in the left guinea pig atrium at a concentration of from $10^{-6}$ to $10^{-4}$ M in accordance with the principles of N. Reuter and E. Heeg [Arch.Pharmakol. 268 (1971) 323–333].

The compounds are therefore useful as antiarrhythmic agents, e.g. for the treatment of heart rhythm disorders.

The compounds also exhibit α-adrenoceptor blocking activity, as indicated by standard tests. For example, the inhibition of α-adrenoceptors may be observed in isolated spiral strips of the Vena femoralis of dogs (E. Müller-Schweinitzer and E. Stürmer, *Br.J.Pharmacol.* [1974] 51, 441–446), at a bath concentration of from about $10^{-7}$ M to about $10^{-5}$ M.

The compounds are therefore useful as α-adrenoceptor blocking agents, e.g. for the prophylaxis and treatment of disorders related to a paralysis of intestine motility, such as paralytic ileus.

The compounds also possess β-adrenoceptor blocking activity, as indicated by standard tests. For example, in the isolated, spontaneously-beating guinea pig atrium (method of K. Saameli, *Helv. Physiol. Acta* 25 [1967] CR 219-CR 221) inhibition of the positive inotropic effect of adrenaline is observed at a bath concentration of about $10^{-9}$ M to about $10^{-6}$ M.

The compounds are therefore useful as β-adrenoceptor blocking agents, e.g. for the prophylaxis and treatment of coronary diseases such as Angina pectoris, of conditions resulting from sympathetic overstimulation, such as nervous heart ailments, of hypertension, of myocardial infarct, for interval migraine treatment, and for the treatment of glaucoma and thyreotoxicosis.

For the above-mentioned antiarrhythmic and α- and β- adrenoceptor blocking uses the dosage will, of course, vary depending on the compound employed, mode of administration and treatment desired. However, in general, satisfactory results are obtained when administered at a daily dosage of from about 0.001 mg to about 100 mg per kg animal body weight, conveniently given in divided doses 2 to 4 times a day or in sustained release form. For the larger mammals, the total daily dosage is in the range of from about 0.1 mg to about 1000 mg, and dosage forms suitable for oral administration comprise from about 0.025 mg to about 500 mg of the compounds admixed with a solid or liquid pharmaceutical carrier or diluent. Examples of daily doses are from 0.1 to 100 mg.

In general, the 2(S) optical isomers of the compounds are more active than the 2(R) optical isomers as β-adrenoceptor-blocking agents.

It will be appreciated that it may be necessary to convert a compound having a substituted hydroxy group in the 2 position of the 3-aminopropoxy side chain to the corresponding free hydroxy compound prior to carrying out the in vitro tests indicated above for showing activity.

The cardiotonic use is the preferred use of the compounds.

The compounds may be administered in pharmaceutically acceptable salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be in the form of, for example, a solution or a tablet.

In a 1st group of compounds $R_1$ is hydrogen.
In a 2nd group of compounds $R_2$ is cyano.
In a 3rd group of compounds $R_2$ is carbamoyl.
In a 4th group of compounds $R_2$ is alkoxycarbonyl.
In a 5th group of compounds R is a group —B—CO—$R_h$.
In a 6th group of compounds B has significance (i).
In a 7th group of compounds B has significance (ii).
In a 8th group of compounds B has significance (iii).
In a 9th group of compounds $R_i$ is hydrogen.
In a 10th group of compounds $R_i$ is alkyl.
In a 11th group of compounds $R_h$ is phenylalkyl.
In a 12th group of compounds $R_h$ is diphenylalkyl.
In a 13th group of compounds R is a group

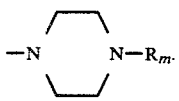

In a 14th group of compounds $R_m$ is a group —CO$R_n$.
In a 15th group of compounds $R_m$ is a group —$R_p$.

In a 16th group of compounds $R_n$ is diphenylalkyl.
In a 17th group of compounds $R_p$ is diphenylalkyl.

I claim:
1. A compound of formula I,

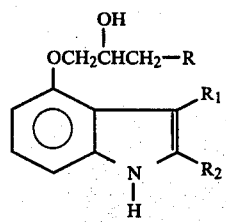

wherein
$R_1$ is hydrogen or methyl,
$R_2$ is cyano and
R is:
(a) a group —B—CO—$R_h$, wherein
B is a group (i), (ii) or (iii), groups (i), (ii) and (iii) having the following significances: (i)

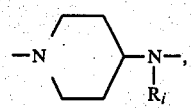

wherein
$R_i$ is hydrogen, alkyl of 1 to 4 carbon atoms, phenyl or phenyl monosubstituted or independently disubstituted by alkyl of 1 to 4 carbon atoms, alkoxy of 1 to 4 carbon atoms or halogen of atomic number of from 9 to 35;
(ii)

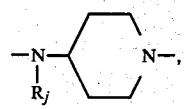

wherein $R_j$ is hydrogen or alkyl of 1 to 4 carbon atoms;
(iii)

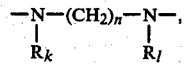

wherein
n is 2, 3 or 4,
$R_k$ is hydrogen or alkyl of 1 to 4 carbon atoms and
$R_l$ has the significance indicated above for $R_i$, and
$R_h$ is phenylalkyl of 7 to 11 carbon atoms or diphenylalkyl of 13 to 17 carbon atoms, any of the phenyl rings of these two groups optionally being mono- or independently disubstituted by alkyl of 1 to 4 carbon atoms, alkoxy of 1 to 4 carbon atoms or halogen of atomic number of from 9 to 35;
(b) a group

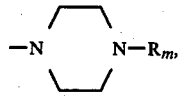

wherein $R_m$ is $-COR_n$ or $-R_p$, wherein
$R_n$ has the significance indicated above for $R_h$ and
$R_p$ is phenyl monosubstituted by alkoxy of 1 to 4 carbon atoms or halogen of atomic number of from 9 to 35, phenyl independently disubstituted by alkyl of 1 to 4 carbon atoms, alkoxy of 1 to 4 carbon atoms or halogen of atomic number of from 9 to 35, phenylalkyl of 7 to 11 carbon atoms or diphenylalkyl of 13 to 17 carbon atoms, any of the phenyl rings of these last two groups optionally being mono- or independently disubstituted by alkyl of 1 to 4 carbon atoms, alkoxy of 1 to 4 carbon atoms or halogen of atomic number of from 9 to 35, and physiologically acceptable hydrolyzable derivatives thereof having the hydroxy group in the 2 position of the 3-aminopropoxy side chain in esterified form, or a pharmaceutically acceptable salt thereof.

2. A pharmaceutical composition comprising a pharmaceutically effective amount of a compound of claim 1 in association with a pharmaceutical carrier or diluent.

3. A method of treating heart insufficiency, which comprises administering to an animal in need of such treatment a therapeutically effective amount of a compound of claim 1.

4. A compound of claim 1 having the formula Ip,

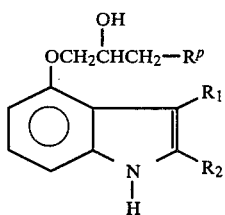

wherein
$R_1$ and $R_2$ are as defined in claim 1 and $R^p$ is:
(a) a group $-B-CO-R_h$, as defined in claim 1;
(b) a group

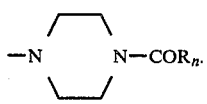

wherein $R_n$ is as defined in claim 1,
or a physiologically acceptable hydrolyzable derivative thereof having the hydroxy group in the 2 position of the 3-aminopropoxy side chain in esterified form.

5. A compound of claim 1 having the formula Ip',

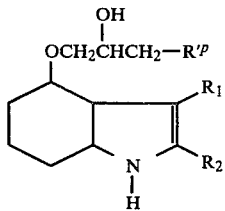

wherein
$R_1$ and $R_2$ are as defined in claim 1 and
$R^{p'}$ is a group

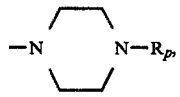

wherein $R_p$ is as defined in claim 1,
or a physiologically acceptable hydrolyzable derivative thereof having the hydroxy group in the 2 position of the 3-aminopropoxy side chain in esterified form.

6. A compound of claim 1 having the formula Ip',

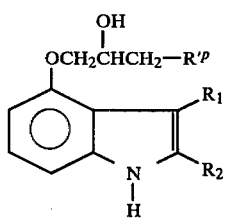

wherein
$R_1$ and $R_2$ are as defined in claim 1 and
$R^{p'}$ is a group

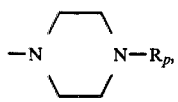

wherein $R_p$ is mono or disubstituted phenyl as defined in claim 1, or is unsubstituted or substituted benzyl, said substitution being as defined in claim 1, or diphenylmethyl, or a physiologically acceptable hydrolyzable derivative thereof having the hydroxy group in the 2 position of the 3-aminopropoxy side chain in esterified form.

7. A compound of claim 1 having the formula Ia,

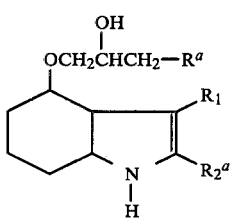

wherein
$R_1$ is as defined in claim 1,
$R_2{}^a$ is cyano and $R^a$ is:
(a) a group $-B^a-CO-R_h{}^a$, wherein $B^a$ is a group

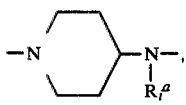

wherein $R_i{}^a$ is hydrogen, methyl, phenyl or halophenyl and $R_h{}^a$ is benzyl or diphenylmethyl;
(b) a group

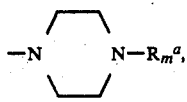

wherein $R_m{}^a$ is $-COR_n{}^a$ or $-R_p{}^a$, wherein $R_n{}^a$ is diphenylmethyl and $R_p{}^a$ is diphenylmethyl or 2,2-diphenylethyl.

8. A compound having formula Ib,

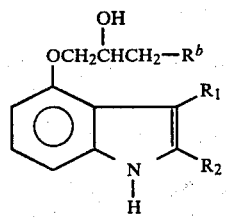

wherein $R_1$ is as defined in claim 1, and $R_2$ is hydrogen, methyl, hydroxymethyl, carboxyl, alkoxycarbonyl of 2 to 5 carbon atoms, carbamoyl or cyano, and $R^b$ is:

(a) a group $-B^b-CO-R_h$, wherein $B^b$ is a group (i'), (ii) or (iii), wherein groups (ii) and (iii) are as defined in claim 1 and group (i') has the following significance:

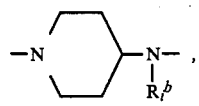

wherein $R_i{}^b$ is hydrogen or alkyl or 1 to 4 carbon atoms, and $R_h$ represents unsubstituted or substituted diphenylalkyl as defined in claim 1, or (b) a group

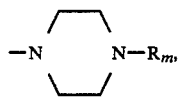

wherein $R_m$ is $-COR_n$ or $-R_p$, wherein $R_n$ and $R_p$ are as defined in claim 1, with the provisos, that (a) when $R_1$ and $R_2$ are hydrogen, then $R_p$ is other than ring substituted or unsubstituted phenethyl and (b) when $R_1$ is hydrogen and $R_2$ is hydrogen, carboxyl or alkoxycarbonyl of 2 to 5 carbon atoms, then $R_p$ is other than monosubstituted phenyl, and physiologically acceptable hydrolyzable derivatives thereof having the hydroxy group in the 2 position of the 3-aminopropoxy side chain in esterified form.

9. A compound of claim 1 having formula Ic,

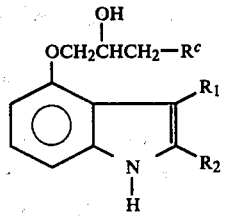

wherein
$R_1$ and $R_2$ are as defined in claim 1 and $R^c$ is:
(a) a group $B^b-CO-R_h{}^b$, wherein $B^b$ is as defined in claim 8 and
$R_h{}^b$ is diphenylalkyl of 13 to 17 carbon atoms, any of the phenyl rings of this group optionally being mono- or independently disubstituted by alkyl of 1 to 4 carbon atoms, alkoxy of 1 to 4 carbon atoms or halogen of atomic number of from 9 to 35;
(b) a group

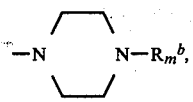

wherein $R_m{}^b$ is $-COR_n{}^b$ or $-R_p{}^b$, wherein $R_n{}^b$ and $R_p{}^b$ have the significance indicated in this claim for $R_h{}^b$, or a physiologically acceptable hydrolyzable derivative thereof having the hydroxy group in the 2 position of the 3-aminopropoxy side chain in esterified form.

10. A compound of claim 8 or 9, wherein $R_2$ is other than hydrogen.

11. A compound of claim 8 or 9 wherein $R_2$ is cyano.

12. A compound of claim 8 or 9 wherein $R_1$ is hydrogen.

13. A compound of claim 8 wherein $R^b$ is a group

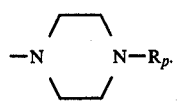

14. A compound of claim 9 wherein $R^c$ is a group

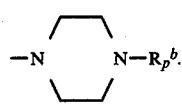

15. A compound of claim 1 having formula E,

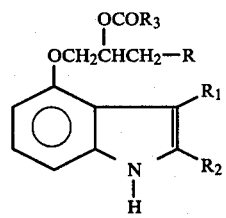

wherein
$R_1$, $R_2$ and R are as defined in claim 1, and $R_3$ is alkyl of 1 to 12 carbon atoms, cycloalkyl of 3 to 7 carbon atoms, phenyl, phenylalkyl of 7 to 12 carbon atoms, phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

16. A compound of claim 1, wherein $R_1$ is hydrogen.

17. A compound of claim 1, wherein R is a group

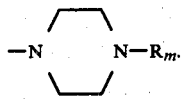

18. A compound of claim 1, wherein B is a group (i).

19. A compound of claim 1, wherein $R_h$, $R_n$ or $R_p$ is substituted or unsubstituted diphenylalkyl.

20. The compound of claim 1, which is 4-[3-(4-diphenylmethylpiperazin-1-yl)-2-hydroxypropoxy]-1H-indol-2-carbonitrile.

21. The compound of claim 8, wherein $R_b$, $R_1$ and $R_2$ respectively are 4-diphenylmethylpiperazin-1-yl, H and $CH_3$.

22. The compound of claim 1, wherein R and $R_1$ respectively are 4-diphenylacetylaminopiperidin-1-yl and H.

23. The compound of claim 1, wherein R and $R_1$ respectively are 4-(N-diphenylacetyl-N-methylamino)-piperidin-1-yl and H.

24. The compound of claim 1, wherein R and $R_1$ respectively are 4-diphenylacetylpiperazin-1-yl and H.

25. The compound of claim 1, wherein R and $R_1$ respectively are 4-[N-(4-chlorophenyl)-N-phenylacetylamino]piperidin-1-yl and H.

26. The compound of claim 1, wherein R and $R_1$ respectively are 4-(diphenylmethyl)piperazin-1-yl and $CH_3$.

27. The compound of claim 8, wherein $R_b$, $R_1$ and $R_2$ respectively are 4-(diphenylmethyl)piperazin-1-yl, H and $CONH_2$.

28. The compound of claim 8, wherein $R_b$, $R_1$ and $R_2$ respectively are 4-(diphenylmethyl)piperazin-1-yl, H and $COOCH_2CH_3$.

29. The compound of claim 1, wherein R and $R_1$ respectively are 4-(2,2-diphenylethyl)-piperazin-1-yl and H.

* * * * *